United States Patent [19]

Maemoto et al.

[11] Patent Number: 5,223,647
[45] Date of Patent: Jun. 29, 1993

[54] CHEMICAL MODIFICATION METHOD OF DIASTEREOMER AND SEPARATION METHOD THEREOF

[75] Inventors: Shunich Maemoto; Akira Iwasaki, both of Takasago; Junzo Hasegawa, Akashi, all of Japan

[73] Assignee: Kanegafuchi Kagaku Kogyo Kabushiki Kaisha, Osaka, Japan

[21] Appl. No.: 902,734

[22] Filed: Jun. 23, 1992

[30] Foreign Application Priority Data

Jun. 25, 1991 [JP] Japan .................................. 3-181958
Sep. 11, 1991 [JP] Japan .................................. 3-261003

[51] Int. Cl.$^5$ .................................. C07C 45/85
[52] U.S. Cl. .................................. 568/366
[58] Field of Search .................................. 568/366, 376

[56] References Cited

U.S. PATENT DOCUMENTS 4,072,715 2/1978 Boguth et al. .................................. 568/376

Primary Examiner—James H. Reamer
Attorney, Agent, or Firm—Armstrong, Westerman, Hattori, McLeland & Naughton

[57] ABSTRACT

The present invention discloses a separating and purifying (4R, 6R)-4-hydroxy-2,2,6-trimethyl cyclohexanone comprising the steps of:

reacting a diastereomer mixture of (4R, 6R)-4-hydroxy-2,2,6-trimethyl cyclohexanone represented by the formula (I)

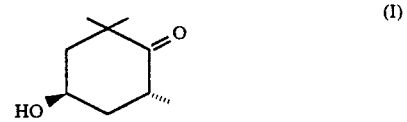

and (4S, 6R)-4-hydroxy-2,2,6-trimethyl cyclohexanone represented by the formula (II)

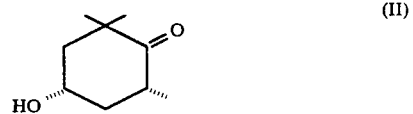

with a reagent which reacts with the hydroxyl groups at least equimolar to the compound represented by the formula (II) to thereby convert the compound represented by the formula (II) into (4S, 6R)-4-hydroxy-2,2,6-trimethyl cyclohexanone derivative represented by the formula (III)

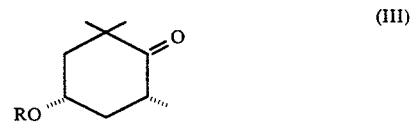

(where R represents a group modifying the hydroxyl group) by modification with priority of the hydroxyl group in the formula (II), and separating the compound of the formula (I) from the compound of the formula (III) through the difference in solubility to water or an organic solvent. According to the invention, (4R, 6R)-4-hydroxy-2,2,6-trimethyl cyclohexanone is easily separated with a high yield.

2 Claims, No Drawings

CHEMICAL MODIFICATION METHOD OF DIASTEREOMER AND SEPARATION METHOD THEREOF

BACKGROUND OF THE INVENTION

1. Field of the Invention

The present invention relates to separation and purification of (4R, 6R)-4-hydroxy-2,2,6-trimethyl cyclohexanone, which is useful as a material for synthesis of optically active compounds such as pigments, from a mixture of (4R, 6R)-4-hydroxy-2,2,6-trimethyl cyclohexanone and its diastereomer (4S, 6R)-4-hydroxy-2,2,6-trimethyl cyclohexanone.

2. Description of the Prior Art

As a method of separating (4R, 6R)-4-hydroxy-2,2,6-trimethyl cyclohexanone from its diastereomer mixture with (4S, 6R)-4-hydroxy-2,2,6-trimethyl cyclohexanone, there has been known, among others, a method of separation by silica gel column chromatography, a method of separation by counter current distribution and a method of separation by crystallization (Japanese Patent Publication No. 7277/'83).

These separation methods, however, had a number of shortcomings such as requiring a large amount of silica gel and eluent and, in case of the counter current distribution method, a large amount of a highly dangerous solvent such as ether. In case of the crystallization method, a solvent such as ether and an extremely low temperature of approximately −70° C. are required, the product obtainable by the crystallization method is poor and several times of recrystallization are essential, which results in a poor recovery percentage, and thus the method hardly can be said to be economical. Accordingly, there has been a strong need for a separation method industrially advantageous.

SUMMARY OF THE INVENTION

It is an object of the present invention to provide a chemical modification method for modifying (4S, 6R)-4-hydroxy-2,2,6-trimethyl cyclohexanone preferentially to (4R, 6R)-4-hydroxy-2,2,6-trimethyl cyclohexanone from a diastereomer mixture of the two.

It is another object of the present invention to provide a method for separating and purifying (4R, 6R)-4-hydroxy-2,2,6-trimethyl cyclohexanone easily with a high yield.

Other objects and advantages of the present invention will be apparent from the detailed description below.

In an attempt to attain the above objects, the present inventors have made intensive studies for developing an economical separation and purifying method for optically active (4R, 6R)-4-hydroxy-2,2,6-trimethyl cyclohexanone and have discovered that the recovery of unreacted (4R, 6R)-4-hydroxy-2,2,6-trimethyl cyclohexanone can be accomplished easily with a high yield by reacting a diastereomer mixture of (4R, 6R)-4-hydroxy-2,2,6-trimethyl cyclohexanone and (4S, 6R)-4-hydroxy-2,2,6-trimethyl cyclohexanone with a reagent capable of reacting with hydroxyl groups in an amount not less than equimolar to (4S, 6R)-4-hydroxy-2,2,6-trimethyl cyclohexanone to thereby modify the hydroxyl groups of (4S, 6R)-4-hydroxy-2,2,6-trimethyl cyclohexanone with priority to convert it into a derivative to increase the difference in polarity from (4R, 6R)-4-hydroxy-2,2,6-trimethyl cyclohexanone, and thus completed the invention.

DETAILED DESCRIPTION OF THE INVENTION

The present invention is, in one aspect, to provide a chemical modification method which comprises reacting a diastereomer mixture of (4R, 6R)-4-hydroxy-2,2,6-trimethyl cyclohexanone represented by the formula (I)

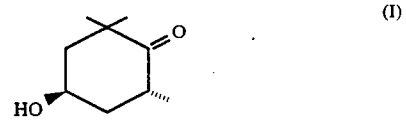

and (4S, 6R)-4-hydroxy-2,2,6-trimethyl cyclohexanone represented by the formula (II)

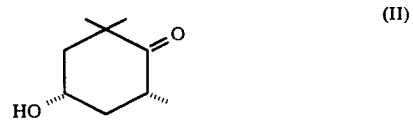

with a reagent which reacts with hydroxyl group at least equimolar to the compound represented by the formula (II) to thereby convert the compound represented by the formula (II) into (4S, 6R)-4-hydroxy-2,2,6-trimethyl cyclohexanone derivative represented by the formula (III)

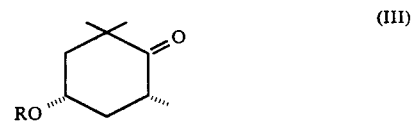

(where R represents a group modifying the hydroxyl group), by modification with priority of the hydroxyl group in the formula (II) substantially without modification of the hydroxyl group in the formula (I).

The present invention is, in another aspect, to provide a method for separating and purifying (4R, 6R)-4-hydroxy-2,2,6-trimethyl cyclohexanone comprising the steps of:

reacting a diastereomer mixture of (4R, 6R)-4-hydroxy-2,2,6-trimethyl cyclohexanone represented by the formula (I)

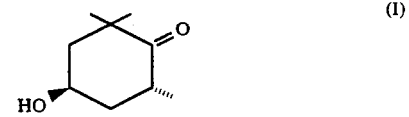

and (4S, 6R)-4-hydroxy-2,2,6-trimethyl cyclohexanone represented by the formula (II)

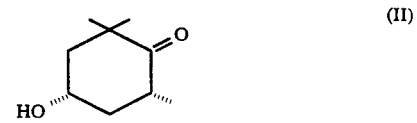

with a reagent which reacts with the hydroxyl groups at least equimolar to the compound represented by the formula (II) to thereby convert the compound represented by the formula (II) into (4S, 6R)-4-hydroxy- 2,2,6-trimethyl cyclohexanone derivative represented by the formula (III)

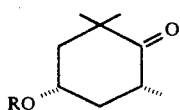

(where R represents a group modifying the hydroxyl group) by modification with priority of the hydroxyl group in the formula (II), and separating the compound of the formula (I) from the compound of the formula (III) through the difference in solubility to water or an organic solvent.

As the reagent for reaction with hydroxyl groups under basic conditions may be used, for example, alkoxyalkyl chlorides such as methoxymethyl chloride, t-buthoxymethyl chloride, 2-methoxyethoxymethyl chloride, 1-ethoxyethyl chloride; alkyl- or arylsilyl chlorides such as trimethylsilyl chloride, triethylsilyl chloride, t-butyldimethylsilyl chloride, isopropyldimethylsilyl chloride, t-butyldiphenysilyl chloride; alkyl- or arylsulfonyl chlorides such as methanesulfonyl chloride, ethanesulfonyl chloride, p-methylphenylsulfonyl chloride, phenylsulfonyl chloride, benzylsulfonyl chloride; alkanoyl chlorides such as acetyl chloride, propanoyl chloride, butanoyl chloride, pentanoyl chloride, hexanoyl chloride, 2-methylpropanoyl chloride, pivaloyl chloride, 3-methylbutanoyl chloride, 3,3-dimethylbutanoyl chloride; unsubstituted or substituted benzoyl chlorides such as benzoyl chloride, 2-methylbenzoyl chloride, 2-chlorobenzoyl chloride, 2,4-dichlorobenzoyl chloride, 2,6-dichlorobenzoyl chloride, 2-acetoxybenzoyl chloride, 3,4,5-trimethoxybenzoyl chloride; substituted acetyl chlorides such as phenylacetyl chloride, diphenylacetyl chloride; substituted carbonyl chlorides such as cyclohexanecarbonyl chloride, 9-fluorenecarbonyl chloride; acid anhydrides such as acetic anhydride, propionic anhydride, lactic anhydride, valeric anhydride, hexanoic anhydride, benzoic anhydride, succinic anhydride, maleic anhydride, phthalic anhydride, alkyl carbonates such as dimethyl carbonate, diethyl carbonate; alkyl chlorocarbonates such as methyl chlorocarbonate, ethyl chlorocarbonate, and these may be used either singly or in combination of two or more.

For the reaction under acidic conditions can be used, among others, 2,3-dihydrofuran, 3,4-dihydro-2H-pyran, 2-methoxypropene and ethylvinyl ether, and these may be used either singly or in combination of two or more.

The quantity of any such reagents reacting with hydroxyl group may be at least one equivalent per the quantity of (4S, 6R)-4-hydroxy-2,2,6-trimethyl cyclohexanone contained in the mixture of (4R, 6R)-4-hydroxy-2,2,6-trimethyl cyclohexanone and (4S, 6R)-4-hydroxy-2,2,6-trimethyl cyclohexanone. When its quantity used is more than one equivalent, it is advisable to conduct the reaction with its progress being checked by means of gas-chromatography or the like, since, if the reaction time is prolonged, the compound (I) reacts to decrease the recovery percentage of the unconverted compound (I) with increasing length of the reaction time.

The reaction may be conducted in various solvents such as methylene chloride, hexane, acetonitrile, ethyl acetate, benzene, toluene, xylene, acetone, tetrahydrofuran, isopropylether, ethylether and dimethylformamide, and these may be used either singly or in combination of two or more.

When the reaction is conducted under basic conditions, there may be used as base, for example, nitrogen-containing heterocyclic compounds such as pyridine, 4-dimethylaminopyridine, imidazole, picoline, lutidine, collidine; aromatic amines such as N, N-dimethylaniline; tertiary amines such as triethylamine, trimethylamine; tetramethyl urea and sodium hydrogencarbonate, and these may be used either singly or in combination of two or more.

The reaction may be conducted by dissolving the mixture of (4R, 6R)-4-hydroxy-2,2,6-trimethyl cyclohexanone and (4S, 6R)-4-hydroxy-2,2,6-trimethyl cyclohexanone in a solvent and adding a reagent reactive with hydroxyl group dropwise or otherwise or dripping its solution in a solvent after addition of a base.

When the reaction is conducted under acidic conditions, use of a catalyst is essential. Examples of the catalyst are pyridinium p-toluenesulfonate, p-toluenesulfonic acid, hydrochloric acid, sulfuric acid, phosphoric acid and their salts, and these may be used either singly or in combination of two more. The quantity of the catalyst may be in a range of 0.001~0.5 equivalent.

The reaction may be conducted by dissolving the mixture of (4R, 6R)-4-hydroxy-2,2,6-trimethyl cyclohexanone and (4S, 6R)-4-hydroxy-2,2,6-trimethyl cyclohexanone in a solvent and adding a proper catalyst after addition of a reagent reactive with hydroxyl group.

The reaction temperature is variable according to the kind of the solvent or the catalyst used, but may be in a range of from −70° C. to a reflux temperature of the solvent. Generally, the lower the reaction temperature, the larger the difference in reaction rate between (4R, 6R)-4-hydroxy-2,2,6-trimethyl cyclohexanone and (4S, 6R)-4-hydroxy-2,2,6-trimethyl cyclohexanone.

The reaction time, too, is variable depending on such factors as the kind of the reagent reactive with hydroxyl group, solvent, base, catalyst used and the quantities and the temperatures thereof, but may generally be in a range of 1~100 hours. If the reaction rate is too low, the reaction may be accelerated by addition of an excessive quantity of the reagent reactive with hydroxyl groups.

It is sometimes the case that derivatives (IV) of (4R, 6R)-4-hydroxy-2,2,6-trimethyl cyclohexanone with its hydroxyl group modified occur, but this has no particular influence on the present invention, except for a slight drop of recovery percentage of the compound (I) since such derivatives can be removed by the method described later.

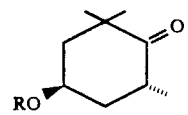

The reaction can be stopped by, for example, adding a saturated aqueous solution of sodium bicarbonate with the progress thereof being confirmed by means of, for example, gas chromatography.

If, in conducting the reaction described above, a large amount of a strong base or acid should be used, the 6th-positioned methyl group of (4R, 6R)-4-hydroxy-2,2,6-trimethyl cyclohexanone and (4S, 6R)-4-hydroxy-2,2,6-trimethyl cyclohexanone is racemized to form (4R, 6S) or (4S, 6S) isomers. This results in a decrease in recovery percentage of (4R, 6R) isomer and, worse, an enantiomer is produced as the reaction product.

Then, the separation and purifying method will be described.

After stopping the reaction by addition of an aqueous solution of sodium bicarbonate to the liquid reactant, the organic phase is first separated and then extraction is made from the aqueous phase by the use of an organic solvent. Then, the organic phase is washed with an acidic aqueous solution or an aqueous solution of copper sulfate for the removal of the base contained in the organic phase. Thereafter, (4R, 6R)-4-hydroxy-2,2,6-trimethyl cyclohexanone once dissolved in the aqueous phase is re-extracted with the organic solvent. By mixing all organic phases and concentrating them under reduced pressure, a crude reaction product containing the compounds (I), (III) and (IV) can be obtained. When the removal of the base is made by the concentration under reduced pressure, a crude reaction product containing the compounds (I), (III) and (IV) can be obtained as the condensate. If the product obtained contains the compound (I) only, not containing (III) and (IV), the subsequent procedure is not necessary.

The crude product is first dissolved in organic solvent-water and after separation of the water phase, re-extraction is done from the organic phase using water. The organic solvent is required to be efficient for extraction of the compounds (III) and (IV) but less suited for extraction of the compound (I). As such solvents, pentane, hexane, heptane, cyclohexane, benzene, toluene, xylene, petroleum ether and mixtures thereof may be used. The aqueous phases obtained are then mixed and the compound (I) is then extracted with ethyl acetate or the like for subsequent dissolving in the organic phase. The organic phase may then be dried by the use of sodium sulfate anhydride or the like and (4R, 6R)-4-hydroxy-2,2,6-trimethyl cyclohexanone is obtainable after subsequent filtration and concentration.

When maleic anhydride, phthalic anhydride or the like is used as a reagent for reaction with hydroxyl group, water is first added to the liquid reactant to stop the reaction, then the organic phase is separated and thereafter the extraction is made using an organic solvent. All organic phases are mixed and then concentrated under reduced pressure to obtain a product containing the compound (I).

The present invention may hereinafter be described in greater detail referring to examples but it is to be noted that the present invention is in no way limited thereto.

EXAMPLE 1

10 g (64 mmol) of a mixture (80:20) of (4R, 6R)-4-hydroxy-2,2,6-trimethyl cyclohexanone and (4S, 6R)-4-hydroxy-2,2,6-trimethyl cyclohexanone were dissolved in 200 ml of methylene chloride, then 4.0 g (51 mmol) of pyridine were added under stirring at $-30°$ C. and then 5.9 g (42 mmol) of benzoyl chloride were added dropwise. Next, 200 ml of a saturated aqueous solution of sodium bicarbonate were added after stirring for 20 hours at $-30°$ C. and after separation of the organic phase, the extraction was conducted from the aqueous phase 3 times using 200 ml of ethyl acetate. The organic phases thus separated were then mixed, dried over sodium sulfate anhydride, filtered and concentrated under reduced pressure for removal of pyridine.

The resulting oily substance was dissolved in 1 liter of water and 1 liter of hexane and after separation of aqueous phase, the remainder was extracted from the hexane phase using another 1 liter of water. From the resulting 2 liters of the aqueous phase, extraction was done 3 times using 2 liters of ethyl acetate and 4.8 g (recovery: 48%) of 4-hydroxy-2,2,6-trimethyl cyclohexanone was obtained after drying over sodium sulfate anhydride, filtration and concentration under reduced pressure. The result of analysis made by gas-chromatography showed that the diastereomer purity was 100%.

Conditions of gas-chromatography analysis: OV-210, 10%/Uniport HP, mesh 80/100, 2 m×3 mm, 100° C., $N_2$, 0.6 kg/cm$^2$ Recovery (%): [Recovered (4R, 6R)+(4S, 6R)-4-hydroxy-2,2,6-trimethyl cyclohexanone]/[(4R, 6R)+(4S, 6R)-4-hydroxy-2,2,6-trimethyl cyclohexanone used as a material]×100

Diastereomer purity (%): [(4R, 6R)-4-hydroxy-2,2,6-trimethyl cyclohexanone/[(4R, 6R)+(4S, 6R)-4-hydroxy-2,2,6-trimethyl cyclohexanone]×100

EXAMPLE 2

1.0 g (6.4 mmol) of a mixture (80:20) of (4R, 6R)-4-hydroxy-2,2,6-trimethyl cyclohexanone and (4S, 6R)-4-hydroxy-2,2,6-trimethyl cyclohexanone was dissolved in 20 ml of methylene chloride, then 0.27 g (3.2 mmol) of pyridine was added under stirring at $-30°$ C. and thereafter 0.38 g (2.7 mmol) of benzoyl chloride was added dropwise. After stirring for 20 hours at $-30°$ C., 20 ml of a saturated aqueous solution of sodium bicarbonate were added. After separation of the organic phase, extraction was done 3 times from the aqueous phase using 20 ml of ethyl acetate. The organic phases were mixed, dried over sodium sulfate anhydride, filtered and then concentrated under reduced pressure for the removal of pyridine.

The oily substance obtained was dissolved in 100 ml of water and 100 ml of hexane and after separation of the aqueous phase, extraction was done once from the hexane phase using 100 ml of water. From the resulting 200 ml of the aqueous phase, extraction was done 3 times and after drying over sodium sulfate anhydride, filtration and concentration under reduced pressure, 0.63 g (recovery: 63%) of 4-hydroxy-2,2,6-trimethyl cyclohexanone was obtained. The result of gas-chromatography analysis showed that the diastereomer purity was 98%.

EXAMPLE 3

An experiment was made in the same way as in Example 2, except that the quantities of pyridine and benzoyl chloride were changed to 0.21 g (2.7 mmol) and 0.31 g (2.2 mmol), respectively. The quantity of 4-hydroxy-2,2,6-trimethyl cyclohexanone obtained was 0.71 g (recovery: 0.71%). The result of gas-chlomatography analysis showed that the diastereomer purity was 96%.

EXAMPLE 4

Experiments were made in the same way as in Example 2, except that 2-methyl propanoyl chloride, pivaroyl chloride, 3-methylbuthanoyl chloride, 2-methylbenzoyl chloride, 2-chlorobenzoyl chloride and 2-acetoxybenzoyl chloride were used, respectively, as acid chlorides instead of benzoyl chloride. The results were as shown in Table 1.

EXAMPLE 5

Experiments were made in the same way as in Example 2, except that hexane, acetonitrile, ethyl acetate and toluene were used, respectively, as solvents instead of methylene chloride. The results were as shown in Table 2.

EXAMPLE 6

Experiments were made in the same way as in Example 2, except that triethylamine was used as a base instead of pyridine and the reaction temperature was changed from −30° C. to 15° C. and 0° C., respectively. The results were as shown in Table 3.

EXAMPLE 7

Experiments were made in the same way as in Example 2, except that the reaction temperature was changed to 15° C., 0° C., −15° C. and −60° C., respectively. The results were as shown in Table 4.

In Tables 1~4, HTH represents 4-hydroxy-2,2,6-trimethyl cyclohexanone.

TABLE 1

| | o-tolyl COCl | o-chlorobenzoyl COCl | o-acetoxybenzoyl COCl | t-Bu COCl | isopropyl COCl | isobutyl COCl |
|---|---|---|---|---|---|---|
| Temperature(°C.) | −30 | −30 | −30 | 10 | −30 | −30 |
| Acid chloride(g) | 0.59 | 0.67 | 0.99 | 0.82 | 0.45 | 0.36 |
| (mmol) | 3.8 | 3.8 | 5.0 | 6.8 | 4.2 | 2.9 |
| Pyridine(g) | 0.36 | 0.36 | 0.47 | 0.65 | 0.40 | 0.28 |
| (mmol) | 4.6 | 4.6 | 6.0 | 8.2 | 5.0 | 3.5 |
| Reaction time(hr) | 28 | 21 | 20 | 48 | 22 | 26 |
| Recovered HTH(g) | 0.56 | 0.55 | 0.50 | 0.27 | 0.41 | 0.53 |
| Recovery(%) | 56 | 55 | 50 | 27 | 41 | 53 |
| Diastereomer purity(%) | 98 | 98 | 98 | 98 | 98 | 98 |

TABLE 2

| | Methylene chloride | Hexane | Acetonitrile | Ethyl acetate | Toluene |
|---|---|---|---|---|---|
| Temperature (°C.) | −30 | 15 | −30 | −30 | −30 |
| Acid chloride (g) | 0.38 | 0.61 | 0.67 | 1.15 | 0.83 |
| (mmol) | 2.7 | 4.3 | 4.8 | 8.2 | 5.9 |
| Pyridine (g) | 0.26 | 0.41 | 0.45 | 0.78 | 0.56 |
| (mmol) | 3.2 | 5.2 | 5.8 | 9.8 | 7.1 |
| Reaction time (hr) | 20 | 44 | 20 | 20 | 21 |
| Recovered HTH (g) | 0.63 | 0.52 | 0.58 | 0.50 | 0.57 |
| Recovery (%) | 63 | 52 | 58 | 50 | 57 |
| Diastereomer purity (%) | 98 | 98 | 98 | 98 | 98 |

TABLE 3

| | Pyridine | Triethylamine | Triethylamine |
|---|---|---|---|
| Temperature (°C.) | −30 | 15 | 0 |
| Benzoyl chloride (g) | 0.38 | 0.59 | 0.85 |
| (mmol) | 2.7 | 4.2 | 6.0 |
| Pyridine (g) | 0.26 | 0.51 | 0.73 |
| (mmol) | 3.2 | 5.0 | 7.2 |
| Reaction time (hr) | 20 | 20 | 26 |
| Recovered HTH (g) | 0.63 | 0.63 | 0.66 |
| Recovery (%) | 63 | 63 | 66 |
| Diastereomer purity (%) | 98 | 98 | 98 |

TABLE 4

| | 15° C. | 0° C. | −15° C. | −30° C. | −60° C. |
|---|---|---|---|---|---|
| Benzoyl choloride (g) | 0.72 | 0.58 | 0.54 | 0.38 | 0.43 |
| (mmol) | 5.1 | 4.1 | 3.8 | 2.7 | 3.1 |
| Pyridine (g) | 0.48 | 0.39 | 0.36 | 0.26 | 0.29 |
| (mmol) | 6.1 | 4.9 | 4.6 | 3.2 | 3.7 |
| Reaction time (hr) | 23 | 24 | 20 | 20 | 26 |
| Recovered HTH (g) | 0.41 | 0.50 | 0.58 | 0.63 | 0.67 |
| Recovery (%) | 41 | 50 | 58 | 63 | 67 |
| Diastereomer purity (%) | 98 | 98 | 98 | 98 | 98 |

EXAMPLE 8

10 g (64 mmol) of a mixture (80:20) of (4R, 6R)-4-hydroxy-2,2,6-trimethyl cyclohexanone and (4S, 6R)-4-hydroxy-2,2,6-trimethyl cyclohexanone were dissolved in 100 ml of toluene and this solution, after addition of 2.5 g (26 mmol) of maleic anhydride, was kept at the room temperature under stirring for the dissolution thereof. Then, under stirring at −20° C., 2.9 g (28 mmol) of triethylamine were added dropwise. After further stirring for 24 hours at −20° C., 100 ml of water were added to the liquid reactant for the separation of the toluene phase. Further, extraction was made from the aqueous phase by the use of toluene (100 ml×5). The resulting organic phases were mixed, dried over sodium sulfate anhydride, filtered and concentrated under reduced pressure, and 6.5 g (recovery: 65%) of 4-hydroxy-2,2,6-trimethyl cyclohexanone were thus obtained. The result of the gas-chromatography analysis showed that the diastereomer purity was 98%.

EXAMPLE 9

An experiment was made in the same way as in Example 8, with the reaction temperature changed to 0° C. The quantity of 4-hydroxy-2,2,6-trimethyl cyclohexanone obtained was 7.0 g (recovery: 70%). The diastereomer purity was 96%.

EXAMPLE 10

10 g (64 mmol) of a mixture (80:20) of (4R,6R)-4-hydroxy-2,2,6-trimethyl cyclohexanone and (4S,6R)-4-hydroxy-2,2,6-trimethyl cyclohexanone were dissolved in 100 ml of toluene, then 5.69 g (38.4 mmol) of phthalic anhydride were added and stirring was continued at the room temperature for the dissolution thereof. Then, 4.66 g (46 mmol) of triethylamine were added dropwise at the room temperature. After stirring for 24 hours at the room temperature, 100 ml of water were added to the liquid reactant and the toluene phase was separated. Further, extraction was done from the aqueous phase by the use of toluene (100 ml×5). The resulting organic phases were mixed, dried over sodium sulfate anhydride, filtered and concentrated under pressure and 5.5 g (recovery: 55%) of 4-hydroxy-2,2,6-trimethyl cyclohexanone were thus obtained. The result of the gas-chromatography analysis showed that diastereomer purity was 97%.

As seen from the above, the present invention enables separation of (4R,6R)-4-hydroxy-2,2,6-trimethyl cyclohexanone with a high yield and with ease.

What is claimed is:

1. A method for separating and purifying (4R,6R)-4-hydroxy-2,2,6-trimethyl cyclohexanone, comprising the steps of;

providing a diastereomer mixture of an amount of (4R,6R)-4-hydroxy-2,2,6-trimethyl cyclohexanone of formula I

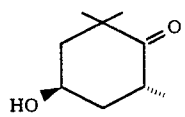

I and an amount of (4S,6R)-4-hydroxy-2,2,6-trimethyl cyclohexanone of formula II

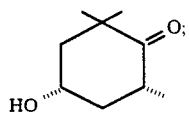

II with an amount of reagent reactive with hydroxyl functional group selected from at least one member of the group consisting of alkoxyalkyl chloride; alkylsilyl chloride; arylsilyl chloride; alkylsulfonyl chloride; arylsulfonyl chloride; alkanoyl chloride; benzoyl chloride; benzoyl chloride substituted with one of methyl, chloro, acetoxy, and alkoxy; acetyl chloride substituted with one of phenyl and diphenyl; carbonyl chloride substituted with one of cyclohexane and fluorene; acid anhydride; alkyl carbonate and alkyl chlorocarbonate, in a solvent under basic conditions, wherein the reagent is used in an at least equimolar to the amount of the (4S,6R)-4-hydroxy-2,2,6-trimethyl cyclohexanone of formula II, the reaction temperature is in a range of about −70° C. to the reflux temperature of the solvent and the reaction rate of (4S,6R)-4-hydroxy-2,2,6-trimethyl cyclohexanone of formula II and the reagent is faster than the reaction rate of (4R,6R)-4-hydroxy-2,2,6-trimethyl cyclohexanone of formula I and the reagent, to preferentially form (4S,6R)-4-hydroxy-2,2,6-trimethyl cyclohexanone derivative represented by the formula III

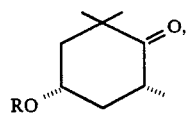

III and R is one of alkoxyalkyl; alkylsilyl; arylsilyl; alkylsulfonyl; arylsulfonyl; alkanoyl; benzoyl; benzoyl substituted with one of methyl, chloro, acetoxy, alkoxy and carboxyl; acetyl substituted with one of phenyl and diphenyl; carbonyl substituted with one of cyclohexane and fluorene; alkanoyl substituted with carboxyl, alkenoyl substituted with carbonyl or alkoxycarbonyl; and separating the (4R,6R)-4-hydroxy-2,2,6-trimethyl cyclohexanone of formula I from the derivative of formula III.

2. A method for separating and purifying (4R,6R)-4-hydroxy-2,2,6-trimethyl cyclohexanone, comprising the steps of;

providing a diastereomer mixture of an amount of (4R,6R)-4-hydroxy-2,2,6-trimethyl cyclohexanone of formula I

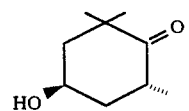

I and an amount of (4S,6R)-4-hydroxy-2,2,6-trimethyl cyclohexanone of formula II

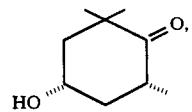

II with an amount of reagent reactive with hydroxyl functional group selected from the group consisting of 2,3-dihydrofuran, 3,4-dihydro-2H-pyran, 2-methoxypropene and ethylvinyl ether, in a solvent under acidic conditions in the presence of an acid catalyst selected from at least one member of the group consisting of pyridinium p-toluenesulfonate, p-toluenesulfonic acid, hydrochloric acid, sulfuric acid, and phosphoric acid, or salts thereof, wherein the reagent is used in at least equimolar to the amount of the (4S,6R)-4-hydroxy-2,2,6-trimethyl cyclohexanone of formula II, the reaction temperature is in a range of about −70° C. to the reflux temperature of the solvent and the reaction rate of (4S,6R)-4-hydroxy-2,2,6-trimethyl cyclohexanone of formula II and the reagent is faster than the reaction rate of (4R,6R)-4-hydroxy-2,2,6-trimethyl cyclohexanone of formula I and the reagent, to preferentially form (4S,6R)-4-hydroxy-2,2,6-trimethyl cyclohexanone derivative represented by the formula III III
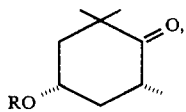
and R is one of 2-tetrahydrofuranyl, 2-tetrahydropyranyl, 2-methoxy-2-propyl, and 1-ethoxy-1-ethyl; and
separating the (4R,6R)-4-hydroxy-2,2,6-trimethyl cyclohexanone of formula I from the derivative of formula III.
* * * * *